(12) United States Patent
Schelberger et al.

(10) Patent No.: US 6,365,613 B1
(45) Date of Patent: Apr. 2, 2002

(54) FUNGICIDAL MIXTURES

(75) Inventors: Klaus Schelberger, Gönnheim; Maria Scherer, Landau; Hubert Sauter, Mannheim; Bernd Müller, Frankenthal; Erich Birner, Altleiningen; Joachim Leyendecker, Ladenburg; Manfred Hampel, Neustadt; Eberhard Ammermann, Heppenheim; Gisela Lorenz, Neustadt; Siegfried Strathmann, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/423,973
(22) PCT Filed: May 18, 1998
(86) PCT No.: PCT/EP98/02942
§ 371 Date: Nov. 17, 1999
§ 102(e) Date: Nov. 17, 1999
(87) PCT Pub. No.: WO98/53688
PCT Pub. Date: Dec. 3, 1998

(30) Foreign Application Priority Data

May 30, 1997 (DE) .......................... 197 22 658

(51) Int. Cl.$^7$ ................... A01N 43/64; A01N 43/52; A01N 43/56; A01N 37/12; A01N 37/18
(52) U.S. Cl. ............... 514/384; 514/388; 514/394; 514/407; 514/478; 514/479; 514/539; 514/619
(58) Field of Search ................ 514/407, 384, 514/388, 394, 478, 479, 539, 619

(56) References Cited

U.S. PATENT DOCUMENTS

| | | | |
|---|---|---|---|
| 4,829,085 A | 5/1989 | Wenderoth et al. | 514/522 |
| 5,395,854 A | 3/1995 | Brand et al. | 514/619 |
| 5,824,705 A | 10/1998 | Mueller et al. | 514/485 |

FOREIGN PATENT DOCUMENTS

| | | |
|---|---|---|
| CA | 2194502 | 1/1996 |
| CA | 2194503 | 1/1996 |
| CA | 2195577 | 2/1996 |
| DE | 19522712 | 1/1997 |
| EP | 0253213 | 1/1988 |
| EP | 0254426 | 1/1988 |
| EP | 0398692 | 11/1990 |
| EP | 0477631 | 4/1992 |
| EP | 0741970 | 11/1996 |
| WO | 93/15046 | 8/1993 |

(List continued on next page.)

OTHER PUBLICATIONS

Tomlin, "The Pesticide Manual Incorporating The Agrochemicals Handbook"; $10^{th}$ Ed. (1995) pp. 82–84, 149, 150, 286, 533, 534, 972, 973 & 987–989.*

Primary Examiner—Allen J. Robinson
(74) Attorney, Agent, or Firm—Keil & Weinkauf

(57) ABSTRACT

A fungicidal mixture comprises
a.1) a phenyl benzyl ether derivative of the formula I.a, I.b or I.c,

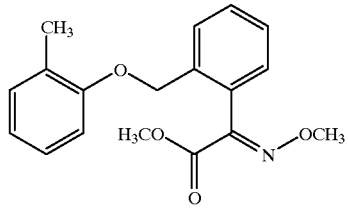

I.a

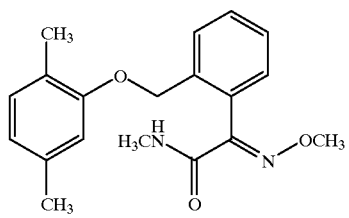

I.b

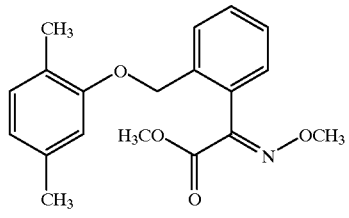

I.c or
a.2) a carbamate of the formula I.d,

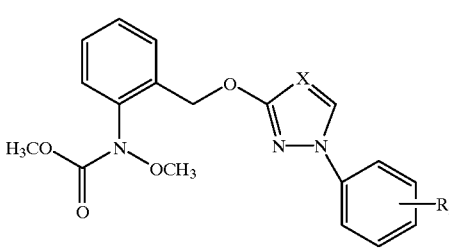

I.d where X is CH and N, n is 0, 1 or 2 and R is halogen, $C_1$–$C_4$-alkyl and $C_1$–$C_4$-haloalkyl, it being possible for the radicals R to be different if n is 2, or a salt or adduct thereof, and b) a fungicidally active compound from the class of the benzimidazoles or benzimidazole-releasing precursors (II), in a synergistically effective amount.

16 Claims, No Drawings

FOREIGN PATENT DOCUMENTS

| | | |
|---|---|---|
| WO | 96/01256 | 1/1996 |
| WO | 96/01258 | 1/1996 |
| WO | 96/063047 | 2/1996 |
| WO | 97/15189 | 5/1997 |

\* cited by examiner

FUNGICIDAL MIXTURES

This application is a 371 of PCT/EP98/62942, filed May 18, 1998.

The present invention relates to a fungicidal mixture which comprises a.1) a phenyl benzyl ether derivative of the formula I.a, I.b or I.c,

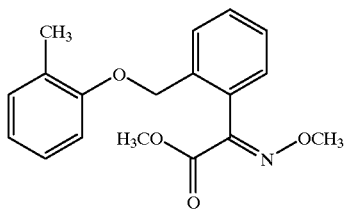
(I.a)

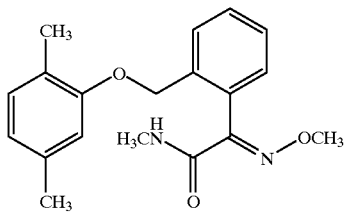
(I.b)

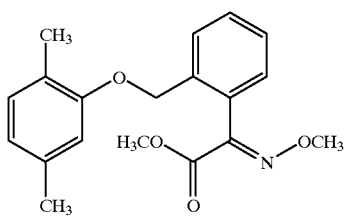
(I.c)

a.2) a carbamate of the formula I.d,

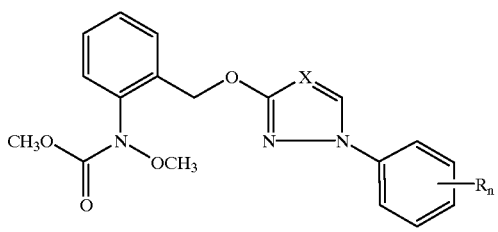
(I.d)

where X is CH and N, n is 0, 1 or 2 and R is halogen, $C_1$–$C_4$-alkyl and $C_1$–$C_4$-haloalkyl, it being possible for the radicals R to be different if n is 2, or a salt or adduct thereof, and b) a fungicidally active compound from the class of the benzimidazoles or benzimidazole-releasing precursors (II), in a synergistically effective amount.

In particular, the invention relates to fungicidal mixtures which contain as benzimidazoles or as benzimidazole-releasing precursor one of the following compounds II.a to II.f:

II.a: methyl 1-(butylcarbamoyl)benzimidazol-2-ylcarbamate

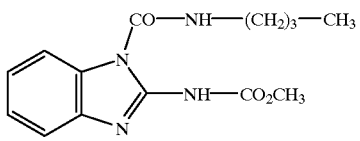
(II.a)

II.b: methyl benzimidazol-2-ylcarbamate

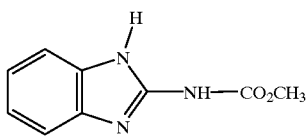
(II.b)

II.c: 2-(2-ethoxyethoxy)ethylbenzimidazol-2-ylcarbamate

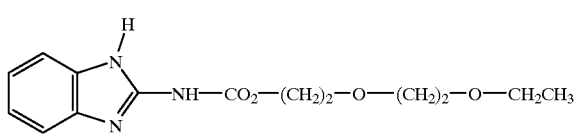
(II.c)

II.d: 2-(2'-furyl)benzimidazole

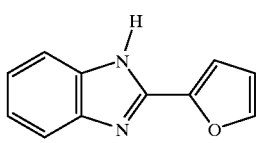
(II.d)

II.e: 2-(1,3-thiazol-4-yl)benzimidazole

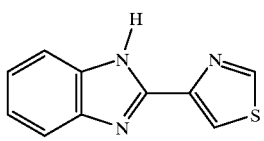
(II.e)

II.f: dimethyl 4,4'-(o-phenylene)bis(3-thioallophanate)

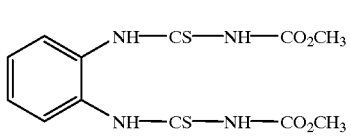
(II.f)

Moreover, the invention relates to methods for controlling harmful fungi using mixtures of the compounds I and II and to the use of the compounds I and the compounds II for preparing such mixtures.

The compounds of the formula I, their preparation and their activity against harmful fungi are disclosed in the literature (EP-A 253 213; EP-A 254 426; EP-A 398 692; EP-A 477 631; WO-A 93/15,046; WO-A 96/01,256; WO-A 96/01,258).

Also disclosed are the compounds II:

II.a (common name: benomyl): U.S. Pat. No. 3,631,176, CAS RN [17804-35-2];

II.b (common name: carbendazim): U.S. Pat. No. 3,657,443, CAS RN [10605-21-7];

II.c (common name: debacarb): CAS RN [62732-91-6];

II.d (common name: fuberidazole): CAS RN [3878-19-1];

II.e (common name: thiabendazole): U.S. Pat. No. 3,017,415, CAS RN [148-79-8], and II.f (common name: thiophanate-methyl): DE-A 19 30 540, CAS RN [123564-05-8].

It is an object of the present invention to provide mixtures which have an improved activity against harmful fungi combined with a reduced total amount of active ingredients applied (synergistic mixtures), with a view to reducing the application rates and improving the activity spectrum of the known compounds I and II.

We have found that this object is achieved by the mixture defined at the outset. Moreover, we have found that applying the compounds I and the compounds II simultaneously, ie. together or separately, or applying the compounds I and the compounds II in succession provides better control of the harmful fungi than is possible with the individual compounds alone.

The formula I.d represents, in particular, carbamates in which the combination of the substituents corresponds to one line of the Table below:

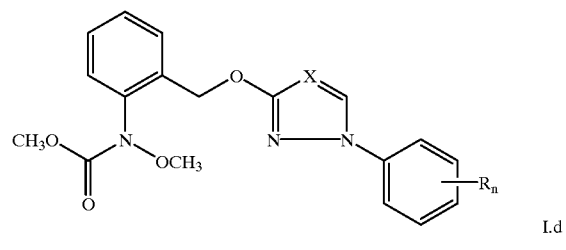

I.d

| No. | X | $R_n$ |
|---|---|---|
| Id.1 | N | 2-F |
| Id.2 | N | 3-F |
| Id.3 | N | 4-F |
| Id.4 | N | 2-Cl |
| Id.5 | N | 3-Cl |
| Id.6 | N | 4-Cl |
| Id.7 | N | 2-Br |
| Id.8 | N | 3-Br |
| Id.9 | N | 4-Br |
| Id.10 | N | 2-$CH_3$ |
| Id.11 | N | 3-$CH_3$ |
| Id.12 | N | 4-$CH_3$ |
| Id.13 | N | 2-$CH_2CH_3$ |
| Id.14 | N | 3-$CH_2CH_3$ |
| Id.15 | N | 4-$CH_2CH_3$ |
| Id.16 | N | 2-$CH(CH_3)_2$ |
| Id.17 | N | 3-$CH(CH_3)_2$ |
| Id.18 | N | 4-$CH(CH_3)_2$ |
| Id.19 | N | 2-$CF_3$ |
| Id.20 | N | 3-$CF_3$ |
| Id.21 | N | 4-$CF_3$ |
| Id.22 | N | 2,4-$F_2$ |
| Id.23 | N | 2,4-$Cl_2$ |
| Id.24 | N | 3,4-$Cl_2$ |
| Id.25 | N | 2-Cl, 4-$CH_3$ |

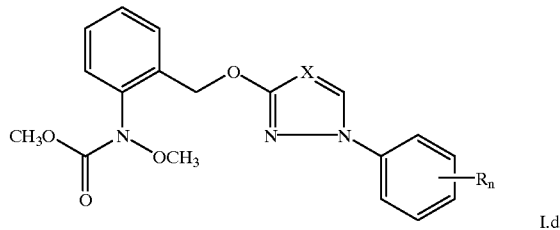

I.d

-continued

| No. | X | $R_n$ |
|---|---|---|
| Id.26 | N | 3-Cl, 4-$CH_3$ |
| Id.27 | CH | 2-F |
| Id.28 | CH | 3-F |
| Id.29 | CH | 4-F |
| Id.30 | CH | 2-Cl |
| Id.31 | CH | 3-Cl |
| Id.32 | CH | 4-Cl |
| Id.33 | CH | 2-Br |
| Id.34 | CH | 3-Br |
| Id.35 | CH | 4-Br |
| Id.36 | CH | 2-$CH_3$ |
| Id.37 | CH | 3-$CH_3$ |
| Id.38 | CH | 4-$CH_3$ |
| Id.39 | CH | 2-$CH_2CH_3$ |
| Id.40 | CH | 3-$CH_2CH_3$ |
| Id.41 | CH | 4-$CH_2CH_3$ |
| Id.42 | CH | 2-$CH(CH_3)_2$ |
| Id.43 | CH | 3-$CH(CH_3)_2$ |
| Id.44 | CH | 4-$CH(CH_3)_2$ |
| Id.45 | CH | 2-$CF_3$ |
| Id.46 | CH | 3-$CF_3$ |
| Id.47 | CH | 4-$CF_3$ |
| Id.48 | CH | 2,4-$F_2$ |
| Id.49 | CH | 2,4-$Cl_2$ |
| Id.50 | CH | 3,4-$Cl_2$ |
| Id.51 | CH | 2-Cl, 4-$CH_3$ |
| Id.52 | CH | 3-Cl, 4-$CH_3$ |

Particular preference is given to the compounds Id.12, Id.23, Id.32 and Id.38.

Owing to the basic character of their nitrogen atoms, the compounds I and II are capable of forming salts or adducts with is inorganic or organic acids or with metal ions.

Examples of inorganic acids are hydrohalic acids such as hydrofluoric acid, hydrochloric acid, hydrobromic acid and hydriodic acid, sulfuric acid, phosphoric acid and nitric acid.

Suitable organic acids are, for example, formic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals with 1 to 20 carbon atoms), arylsulfonic acids or aryldisulfonic acids (aromatic radicals, such as phenyl and naphthyl, which carry one or two sulfo groups), alkylphosphonic acids (phosphonic acids having straight-chain or branched alkyl radicals with 1 to 20 carbon atoms), arylphosphonic acids or aryldiphosphonic acids (aromatic radicals, such as phenyl and naphthyl, which carry one or two phosphonic acid radicals), it being possible for the alkyl or aryl radicals to carry further substituents, eg. p-toluenesulfonic acid, salicylic acid, p-aminosalicylic acid, 2-phenoxybenzoic acid, 2-acetoxybenzoic acid, etc.

Suitable metal ions are, in particular, the ions of the elements of the first to eighth subgroup, in particular chromium, manganese, iron, cobalt, nickel, copper and zinc, and in addition those of the second main group, in particular calcium and magnesium, and of the third and fourth main group, in particular aluminum, tin and lead. The metals can exist, if appropriate, in the various valencies which they can assume.

When preparing the mixtures, it is preferred to employ the pure active ingredients I and II, with which further active ingredients against harmful fungi or other pests, such as insects, arachnids or nematodes, or else herbicidal or growth-regulating active ingredients or fertilizers can be admixed.

The mixtures of the compounds I and II, or the simultaneous, joint or separate use of the compounds I and II, have outstanding action against a wide range of phytopathogenic fungi, in particular from the classes of the Ascomycetes, Basidiomycetes, Phycomycetes and Deuteromycetes. Some of them act systemically and are therefore also suitable for use as foliar and soil-acting fungicides.

They are especially important for controlling a large number of fungi in a variety of crop plants, such as cotton, vegetable species (for example cucumbers, beans, tomatoes, potatoes and cucurbits), barley, grass, oats, bananas, coffee, maize, fruit species, rice, rye, soya, grapevine, wheat, ornamentals, sugar cane, and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, Puccinia species in cereals, Rhizoctonia species in cotton, rice and lawns, Ustilago species in cereals and sugar cane, *Venturia inaequalis* (scab) in apples, Helminthosporium species in cereals, *Septoria nodorum* in wheat, *Botrytis cinerea* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, *Plasmopara viticola* in grapevines, Pseudoperonospora species in hops and cucumbers, Alternaria species in vegetables and fruit, Mycosphaerella species in bananas and Fusarium and Verticillium species.

Furthermore, they can be used in the protection of materials (eg. in the protection of wood), for example against *Paecilomyces variotii*.

The compounds I and II can be applied simultaneously, either together or separately, or in succession, the sequence, in the case of separate application, generally not having any effect on the control results.

The compounds I and II are usually applied in a weight ratio of 10:1 to 0.01:1, preferably 5:1 to 0.05:1, in particular 1:1 to 0.05:1.

Depending on the nature of the desired effect, the application rates of the mixtures according to the invention are, in particular in agricultural crops, from 0.01 to 8 kg/ha, preferably 0.1 to 5 kg/ha, in particular 0.5 to 3.0 kg/ha.

In the case of the compounds I, the application rates are from 0.01 to 2.5 kg/ha, preferably 0.05 to 2.5 kg/ha, in particular 0.1 to 1.0 kg/ha.

Correspondingly, in the case of the compounds II, the application rates are from 0.01 to 10 kg/ha, preferably 0.05 to 5 kg/ha, in particular 0.05 to 2.0 kg/ha.

For seed treatment, the application rates of the mixture are generally from 0.001 to 250 g/kg of seed, preferably 0.01 to 100 g/kg, in particular 0.01 to 50 g/kg.

If phytopathogenic harmful fungi are to be controlled, the separate or joint application of the compounds I and II or of the mixtures of the compounds I and II is effected by spraying or dusting the seeds, the plants or the soils before or after sowing, or before or after plant emergence.

The fungicidal synergistic mixtures according to the invention, or the compounds I and II, can be formulated for example in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should ensure as fine and uniform as possible a distribution of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl, lauryl ethers and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or jointly grinding the compounds I or II or the mixture of the compounds I and II with a solid carrier.

Granules (eg. coated granules, impregnated granules or homogeneous granules) are usually prepared by binding the active ingredient, or active ingredients, to a solid carrier.

Fillers or solid carriers are, for example, mineral earths, such as silicic acids, silica gels, silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise 0.1 to 95% by weight, preferably 0.5 to 90% by weight, of one of the compounds I or II or of the mixture of the compounds I and II. The active ingredients are employed in a purity of from 90% to 100%, preferably 95% to 100% (according to NMR spectrum or HPLC).

The compounds I or II, the mixtures or the corresponding formulations are applied by treating the harmful fungi, their habitat or the plants, seeds, soils, areas, materials or spaces to be kept free from them with a fungicidally effective amount of the mixture, or of the compounds I and II in the case of separate application.

Application can be effected before or after infection by the harmful fungi.

USE EXAMPLE

The synergistic action of the mixtures according to the invention was demonstrated by the following experiments:

Activity against *Botrytis cinerea* on bell peppers

Disks of green bell peppers were sprayed to runoff point with an aqueous preparation of active ingredient which had been prepared from a stock solution comprising 10% of active compound, 63% of cyclohexanone and 27% of emulsifier. 2 hours after the spray coating had dried on, the fruit disks were inoculated with a spore suspension of *Botrytis cinerea* containing 1.7×10⁶ spores per ml of a 2% strength Biomalz solution. The inoculated fruit disks were subsequently incubated in humid chambers at 18° C. for 4 days. The Botrytis infection on the diseased fruit disks was then evaluated visually.

Evaluation was carried out by determining the infected leaf areas in percent. These percentages were converted into efficacies. The efficacy (E) was calculated as follows using Abbot's formula:

$$E=(1-\alpha)\cdot 100/\beta$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active ingredients were determined using Colby's formula [R. S. Colby, weeds 15 (1967), 20–22] and compared with the observed efficacies.

Colby's formula: $E=x+y-x\cdot y/100$

E expected efficacy, expressed in % of the untreated control, when using the mixture of the active ingredients A and B at the concentrations a and b x efficacy, expressed in % of the untreated control, when using the active ingredient A at the concentration a y efficacy, expressed in % of the untreated control, when using the active ingredient B at the concentration b The test results are shown in Tables 2 and 3 below.

TABLE 2

| Ex. | Active ingredient | Concentration of active ingredient in the spray liquor in ppm | Efficacy in % of the untreated control |
|---|---|---|---|
| 1C | Control (untreated) | (100% infection) | 0 |
| 2C | Compound Ia | 50 | 50 |
|  |  | 25 | 30 |
|  |  | 12.5 | 30 |
|  |  | 6.3 | 20 |
| 3C | Compound Ic | 25 | 80 |
|  |  | 12.5 | 50 |
| 4C | Comp. Id.32 from Tab. 1 (=Id.1) | 50 | 50 |
|  |  | 25 | 40 |
|  |  | 12.5 | 30 |
| 5C | Comp. IIa (benomyl) | 12.5 | 20 |
|  |  | 6.3 | 10 |
| 6C | Comp. IIf (thiophanatemethyl) | 50 | 20 |
|  |  | 25 | 0 |
|  |  | 12.5 | 0 |

TABLE 3

| Ex. | Mixture according to the invention | Observed efficacy | Calculated efficacy*) |
|---|---|---|---|
| 7 | 12.5 ppm Ia + 12.5 ppm IIa | 85 | 44 |
| 8 | 6.3 ppm Ia + 6.3 ppm IIa | 80 | 28 |
| 9 | 50 ppm Ia + 50 ppm IIf | 95 | 60 |
| 10 | 25 ppm Ia + 25 ppm IIf | 85 | 30 |
| 11 | 12.5 ppm Ia + 12.5 ppm IIf | 60 | 30 |

TABLE 3-continued

| Ex. | Mixture according to the invention | Observed efficacy | Calculated efficacy*) |
|---|---|---|---|
| 12 | 25 ppm Ic + 25 ppm IIf | 95 | 80 |
| 13 | 12.5 ppm Ic + 12.5 ppm IIf | 70 | 50 |
| 14 | 12.5 ppm Id.1 + 12.5 ppm IIa | 70 | 44 |
| 15 | 50 ppm Id.1 + 50 ppm II.f | 95 | 60 |
| 16 | 25 ppm Id.1 + 25 ppm II.f | 60 | 40 |

*)calculated using Colby's formula

The test results show that the observed efficacy in all mixing ratios is higher than the efficacy calculated beforehand using Colby's formula.

What is claimed is:

1. A fungicidal composition comprising synergistically effective amounts of a) a first active component (I) comprising a compound selected from the group of carbamates of formula I.d,

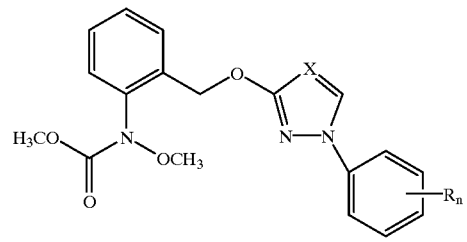

I.d wherein X is CH and N, n is 0, 1 or 2 and R is halogen, C₁–C₄-alkyl and C₁–C₄-haloalkyl, where the radicals R are identical or different when n is 2, and salts and adducts thereof, and b) a second active component (II) comprising a compound selected from the group of fungicidally active benzimidazoles and benzimidazole-releasing compounds.

2. The composition defined in claim 1, wherein the active component (II) is selected from the group of compounds II.a: methyl 1-(butylcarbamoyl)benzimidazol-2-ylcarbamate

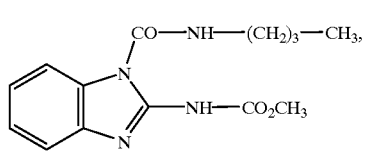

(II.a)

II.b: methyl benzimidazol-2-ylcarbamate

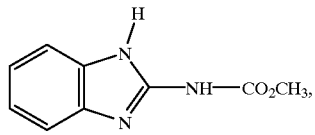

(II.b)

II.c: 2-(2-ethoxyethoxy)ethyl benzimidazol-2-ylcarbamate (II.c)

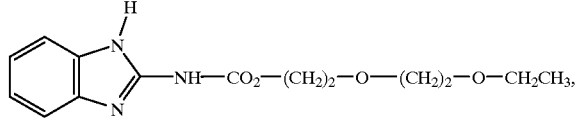

II.d: 2-(2'-furyl)benzimidazole (II.d)

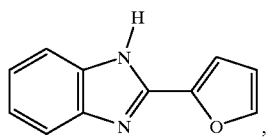

II.e: 2-(1,3-thiazol-4-yl)benzimidazole (II.e)

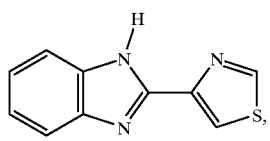

and

II.f: dimethyl 4,4'-(o-phenylene)bis(3-thioallophanate)

(II.f)

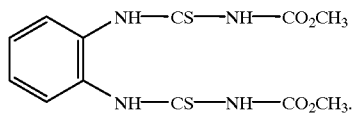

3. The composition defined in claim 1, wherein the weight ratio of component (I) to component (II) is from 10:1 to 0.01:1.

4. The composition defined in claim 1 which is conditioned in two parts, one part comprising the active component (I) in a solid or liquid carrier and the other part comprising the active component (II) in a solid or liquid carrier.

5. The composition defined in claim 1, wherein the active component (I) additionally comprises at least one compound selected from the group consisting of phenyl benzyl ether compounds of formula I.a, formula I.b and formula I.c:

I.a

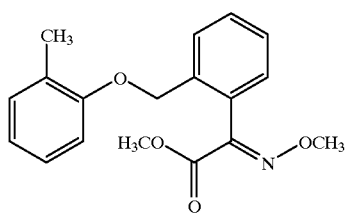

-continued

I.b

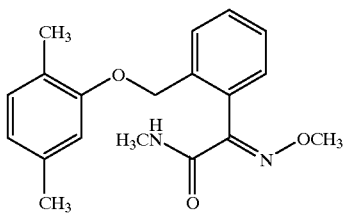

I.c

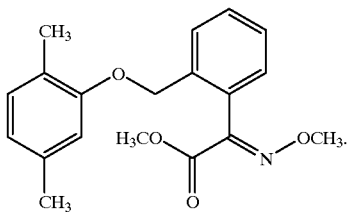

6. The composition defined in claim 5, wherein the active component (II) is selected from the group of compounds II.a: methyl 1-(butylcarbamoyl)benzimidazol-2-ylcarbamate (II.a)

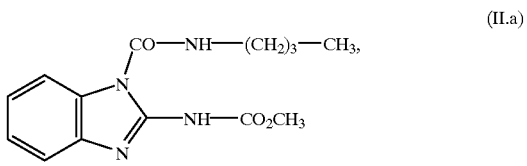

II.b: methyl benzimidazol-2-ylcarbamate (II.b)

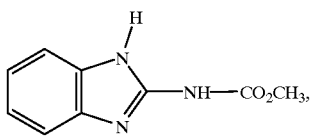

II.c: 2-(2-ethoxyethoxy)ethyl benzimidazol-2-ylcarbamate (II.c)

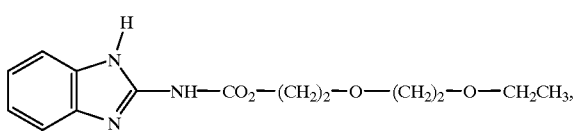

II.d. 2-(2'-furyl)benzimidazole (II.d)

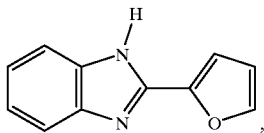

II.e: 2-(1,3-thiazol-4-yl)benzimidazole

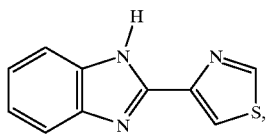
(II.e)

and

II.f: dimethyl 4,4'-(o-phenylene)bis(3-thioallophanate)

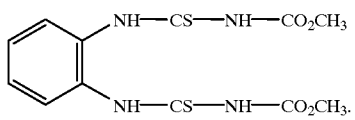
(II.f)

7. The composition defined in claim 5, wherein the weight ratio of component (I) to component (II) is from 10:1 to 0.01:1.

8. The composition defined in claim 5 which is conditioned in two parts, one part comprising the active component (I) in a solid or liquid carrier and the other part comprising the active component (II) in a solid or liquid carrier.

9. A method for controlling harmful fungi, which comprises treating the harmful fungi, their habitat or plants, seeds, soils, areas, materials or spaces to be kept free from said fungi with synergistically effective amounts of the active component (I) and the active component (II) wherein the active components (I) and (II) are as defined in claim 1.

10. The method of claim 9, wherein the active component (I) and the active component (II) are applied simultaneously, either together or separately, or in succession.

11. The method of claim 9, wherein the active component (I) is applied in an amount of from 0.01 to 2.5 kg/ha.

12. The method of claim 9, wherein the active component (II) is applied in an amount of from 0.01 to 10 kg/ha.

13. The method of claim 9, wherein the active component (I) additionally comprises at least one compound selected from the group consisting of phenyl benzyl ether compounds of formula I.a, formula I.b and formula I.c:

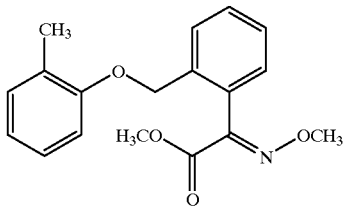
I.a

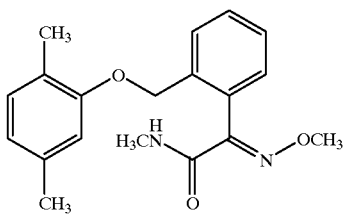
I.b

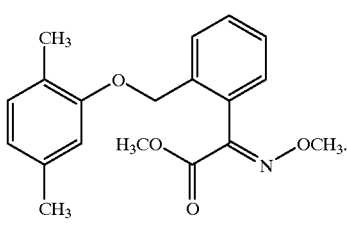
I.c

14. The method of claim 13, wherein the active component (I) and the active component (II) are applied simultaneously, either together or separately, or in succession.

15. The method of claim 13, wherein the active component (I) is applied in an amount of from 0.01 to 2.5 kg/ha.

16. The method of claim 13, wherein the active component (II) is applied in an amount of from 0.01 to 10 kg/ha.

* * * * *